US010520474B2

(12) United States Patent
De Frutos-Galindo et al.

(10) Patent No.: US 10,520,474 B2
(45) Date of Patent: Dec. 31, 2019

(54) INSPECTION TOOL (71) Applicant: AIRBUS OPERATIONS S.L., Madrid (ES)

(72) Inventors: Yolanda De Frutos-Galindo, Madrid (ES); Álvaro Espada Tejedor, Madrid (ES); Carlos Jusdado-Serrano, Madrid (ES)

(73) Assignee: AIRBUS OPERATIONS S.L., Madrid (ES)

( * ) Notice: Subject to any disclaimer, the term of this patent is extended or adjusted under 35 U.S.C. 154(b) by 212 days.

(21) Appl. No.: 15/715,380

(22) Filed: Sep. 26, 2017

(65) Prior Publication Data

US 2018/0088085 A1    Mar. 29, 2018

(30) Foreign Application Priority Data

Sep. 26, 2016 (EP) ..................... 16382447

(51) Int. Cl.
| | | |
|---|---|---|
| *G01N 29/22* | (2006.01) | |
| *B64F 5/60* | (2017.01) | |
| *G01B 21/14* | (2006.01) | |
| *G01N 29/04* | (2006.01) | |
| *G01N 29/24* | (2006.01) | |

(Continued)

(52) U.S. Cl.
CPC ............ *G01N 29/225* (2013.01); *B64F 5/60* (2017.01); *G01B 21/14* (2013.01); *G01N 29/04* (2013.01); *G01N 29/043* (2013.01); *G01N 29/24* (2013.01); *G01N 29/265* (2013.01); *G01N 29/28* (2013.01); *G10K 11/004* (2013.01); *G10K 11/355* (2013.01); *F16C 11/04* (2013.01); *G01N 2291/0234* (2013.01);

(Continued)

(58) Field of Classification Search
CPC .... G01N 29/225; G01N 29/04; G01N 29/043; G01N 29/24; G01N 29/265; G01N 29/28; G01N 2291/0234; G01N 2291/0289; G01N 2291/044; G01N 2291/2634; B64F 5/60; G01B 21/14; G10K 11/004; G10K 11/355; F16C 11/04
USPC ................................. 73/596, 866.5
See application file for complete search history.

(56) References Cited

U.S. PATENT DOCUMENTS 7,543,512 B2    6/2009  Smith et al.
8,161,818 B2 *  4/2012  Elze ..................... G01N 29/043
                                        73/596

(Continued)

FOREIGN PATENT DOCUMENTS

| CN | 104 359 984 | 2/2015 |
| DE | 297 03 255 | 7/1998 |

OTHER PUBLICATIONS

Extended Search Report for EP16382447.7, dated Dec. 12, 2016, 8 pages.

*Primary Examiner* — Lisa M Caputo
*Assistant Examiner* — Rose M Miller
(74) *Attorney, Agent, or Firm* — Nixon & Vanderhye P.C.

(57) ABSTRACT

An inspection tool for inspection of a hole of a metallic lug, including, a first arm, a second arm, a third arm, and a housing element, wherein the first arm, the third arm and the housing element may vary their position independently of each other in relation to the second arm. Also, the present invention discloses an inspection device for inspection of a metallic lug that comprises an inspection tool and a probe housed in the housing element, and a method for detecting cracks around metallic lug.

16 Claims, 8 Drawing Sheets

(51) Int. Cl.
  *G01N 29/28* (2006.01)
  *G01N 29/265* (2006.01)
  *G10K 11/00* (2006.01)
  *G10K 11/35* (2006.01)
  *F16C 11/04* (2006.01)

(52) U.S. Cl.
  CPC ............ *G01N 2291/0289* (2013.01); *G01N 2291/044* (2013.01); *G01N 2291/2634* (2013.01)

(56) References Cited

U.S. PATENT DOCUMENTS

2004/0089082 A1* 5/2004 Gifford ................ G01N 27/902
 73/866.5
2018/0272101 A1* 9/2018 Arnott ................. A61M 16/202
2019/0094187 A1* 3/2019 Takemoto ............ G01N 29/043

\* cited by examiner

INSPECTION TOOL

RELATED APPLICATION

This application claims priority to European Patent Application No. EP16382447.7 filed 26 Sep. 2016, the entirety of which is incorporated by reference.

TECHNICAL FIELD OF THE INVENTION

The present invention belongs to the field of inspection in-service of lugs looking for cracks, particularly, looking for cracks propagating radially from the circumference of the lug's hole and, more particularly, to the field of inspection in-service of lug located on an aircraft.

BACKGROUND OF THE INVENTION

In ordinary inspection of an aircraft, there are some operations for inspection specific structural elements. Until know, looking for cracks are currently performed by shear waves ultrasonic inspection (UT). For example, one technique consists of coupling an UT probe on the surface of a lug in such a way that a UT beam is tangent to the circumference of the lug's hole. The optimum distance to the cracks depends on the lug thickness, the side of the lug where the crack is initiated, the cracks size, the angle of the probe applied on the lug, the probes size and the number of rebounds to reach the crack.

This type of inspection additionally implies a theoretical calculation or modeling of the optimum parameters and practical checking. Also, the inspection of lugs is not a static inspection of one point of the lug, consisting of look for cracks around the lug. This non-static inspection consists of sliding the probe around the circumference of the lug's hole ensuring that distance from the probe to the "expected crack" is kept optimum, and ensuring that UT beam is tangent to the lug circumference.

Unfortunately, it is difficult to comply with the above requirements disclosed. Consequently, dedicated support tools are defined to ensure proper probe sliding on the particular lug configuration. Thus, each operator must manufacture or buy, store and monitor periodically the tools defined in the maintenance manuals in order to perform this type of inspection.

Therefore, there is a need for a particular tool which makes easier and simpler the inspection of lugs, solving the problems of the state of the art.

SUMMARY OF THE INVENTION

The present invention may be applied to solve the aforementioned problems. The invention may be embodied as an inspection tool for inspection a hole of a metallic lug, an inspection device for inspection of metallic lug, and a method for detecting cracks around metallic lug.

In a first embodiment, the invention is an inspection tool for inspection of a hole of a metallic lug, comprising:

(a) a first arm comprising a first lateral part with a first lateral part end, the first lateral part end being configured to be in contact with the hole of the metallic lug, a central part, and a second lateral part with a second lateral part end, the second lateral part end being configured to be in contact with the hole of the metallic lug, the first lateral part and the central part forming an angle (A), the second lateral part and the central part forming an angle, and said central part comprising a guiding cavity, (b) a second arm comprising: a guiding cavity and two ends, each end comprising respective guiding projections, (c) a third arm comprising: a guiding cavity, a first end and a second end, the first end and second end being configured to be in contact with the hole of the metallic lug, and (d) a housing element comprising: a first housing part, a second housing part, and a guiding projection, wherein the first arm, the third arm and the housing element may vary their position independently of each other in relation to the second arm.

Throughout this application, "component" of the tool will be understood as each component part of the tool which are the first arm, the second arm, the third arm and the housing element.

Advantageously, the inspection tool simplifies aircraft inspections, standardizing the usage of a tool (reducing the variety of tools), and ensuring the inspection quality by the essential parameters (inner diameter of the lug's hole, distance between the hole and the probe, distance between the probe and the "expected crack", and distance to fix the tool to the edge of the lug's hole).

Additionally, the inspection tool advantageously provides cost reduction due to no need to manufacture a specific tool for each lug configuration, storage and monitoring reduction, and specially time of inspection reduction.

In a particular embodiment, the guiding projections of the second arm are linked to the first arm and third arm through the guiding cavities of each first and third arm respectively, being such guiding projections configured to slide along said guiding cavities. In other particular embodiment, the guiding projection of the housing element is linked to the second arm through the guiding cavity of the second arm, being such guiding projection configured to slide along said guiding cavity.

Advantageously, these embodiments allow moving and fit the tool on the surface of the lug and around the lug's hole. In this way, each component of the tool can slide on the adjacent component to achieve the necessary adjustment. Also, these embodiments increase the capability of selecting the tool position for inspection around a specific hole, allowing the possibility to modify the position of the tool as needed for each particular case.

In a particular embodiment, the housing element is an interchangeable element. In another embodiment, the first housing part and the second housing part of the housing element are configured to house a probe.

Advantageously, these embodiments allow the possibility to apply different probe sizes or probe types.

In a particular embodiment, the angle formed between the first lateral part and the central part of the first arm is comprised between 100°-115°. In a preferably embodiment, the angle formed between the first lateral part and the central part of the first arm is 108°. In another embodiment, the angle formed between the second lateral part and the central part of the first arm is comprised between 125°-145°. In a preferably embodiment, preferably the angle formed between the second lateral part and the central part of the first arm is 135°.

Advantageously, these ranges of angles, and in particular the preferred angles, allow inspecting the broadest values of the diameter of the lug's hole, which in turn are the most used in the aeronautical field.

In a particular embodiment, each guiding projection comprises respectively at least a fixing element, said fixing elements being configured to fix the guiding projections to the first, second and third arm respectively. Advantageously, this embodiment allows fix each component of the tool with the adjacent component, in such a way that each component of the tool cannot slide with respect to the adjacent component.

In a second inventive aspect, the invention provides an inspection device for inspection of a metallic lug, comprising,
(a) an inspection tool according to any embodiment of the first inventive aspect, and
(b) a probe housed in any of the first or second housing parts of the housing element.

In a particular embodiment, the probe is an ultrasonic probe. In a more particular embodiment, the probe is a micro-miniature ultrasonic probe. Advantageously, this type of probes has a small size, which allows the inspection of a high range of diameters of the lug's hole.

In a third inventive aspect, the invention provides a method for detecting cracks around metallic lug comprising the following steps:
(a) measuring the diameter of a hole of the metallic lug,
(b) providing an inspection device according to any embodiment of the second inventive aspect,
(c) positioning and regulating the inspection device around the hole of the metallic lug,
(d) sliding the inspection device around the hole of the lug, and
(e) detecting cracks.

Advantageously, this method allows the possibility to modify the position of the tool as needed for each particular case. Thus depending on the diameter of the leg's hole to be inspected, the tool is adjusted. This method ensures that the inspector slides the probe around the hole at the optimal position for looking for the crack.

In a particular embodiment, the method further comprises applying a couplant on a surface of the lug before step d). Advantageously, this embodiment improves inspection with an ultrasonic probe.

All the features described in this specification (including the claims, description and drawings) and/or all the steps of the described method can be combined in any combination, with the exception of combinations of such mutually exclusive features and/or steps.

DESCRIPTION OF THE DRAWINGS

These and other characteristics and advantages of the invention will become clearly understood in view of the detailed description of the invention which becomes apparent from a preferred embodiment of the invention, given just as an example and not being limited thereto, with reference to the drawings.

DETAILED DESCRIPTION OF THE INVENTION

Once the object of the invention has been outlined, specific non-limitative embodiments are described hereinafter.

Figure 1:
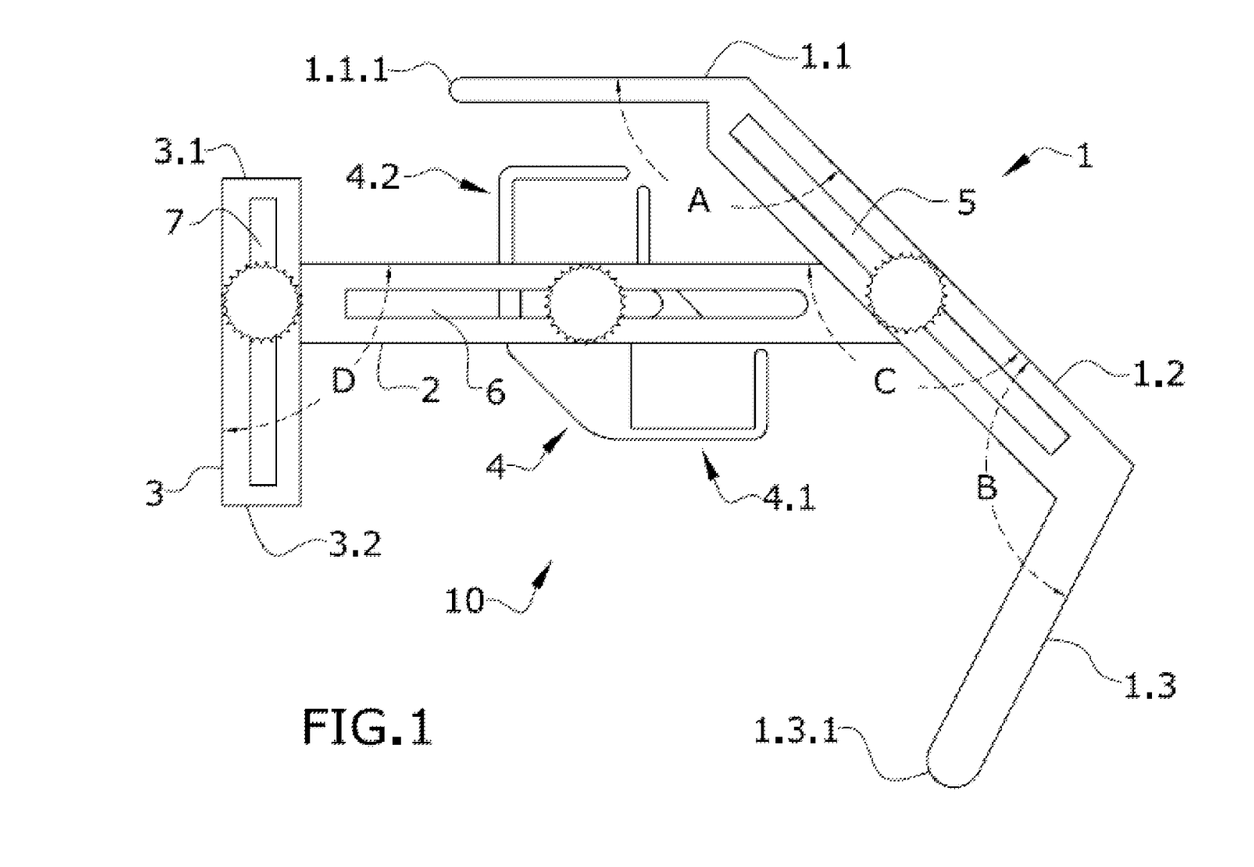
FIG. 1 shows a plan view of the inspection tool according to the present invention.
Figure 2:
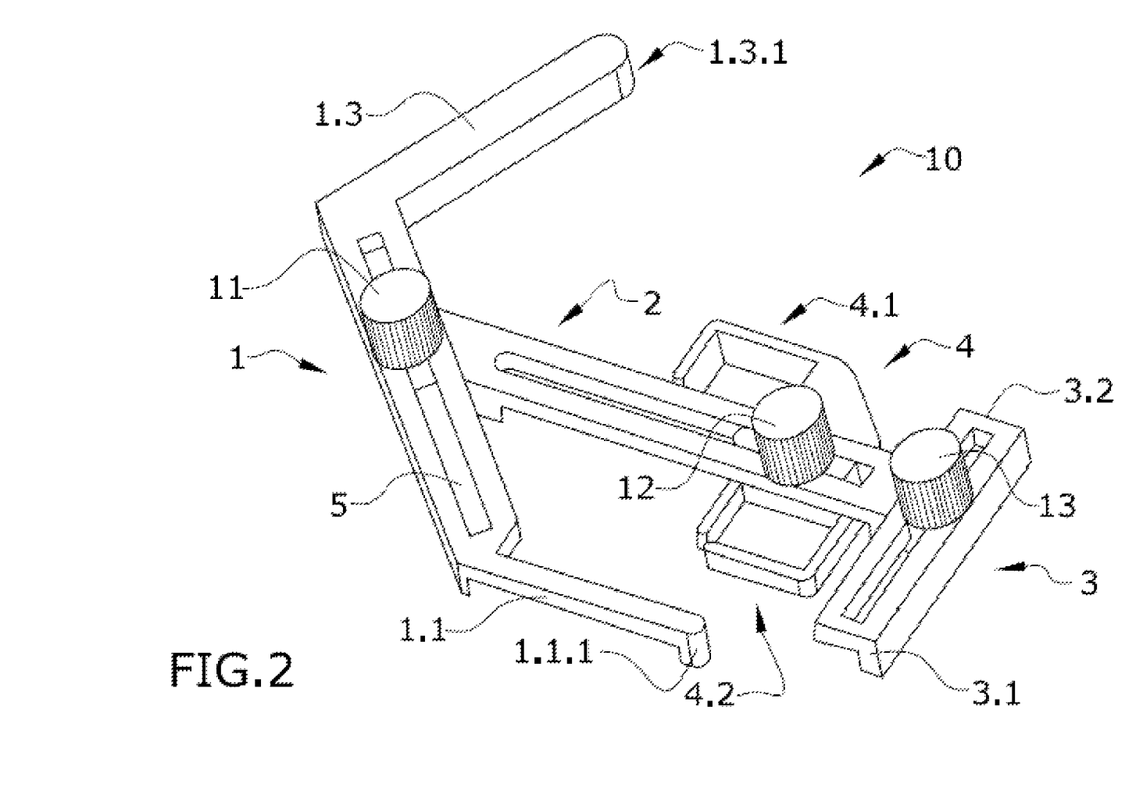
FIG. 2 shows a perspective view of the inspection tool according to the present invention.

FIGS. 1 and 2 show an inspection tool (10) for inspection of a hole (15) of a metallic lug (18) that comprises a first arm (1), a second arm (2), a third arm (3) and a housing element (4).

The first arm (1) comprises a first lateral part (1.1), a central part (1.2) and a second lateral part (1.3), comprising the central part (1.2) a guiding cavity (5). Additionally, the second and third arm (2, 3) comprises a guiding cavity (6, 7) respectively. The cavities located in each arms allow the movement of each component (1, 2, 3, and 4) of the tool (10).

Figure 4:
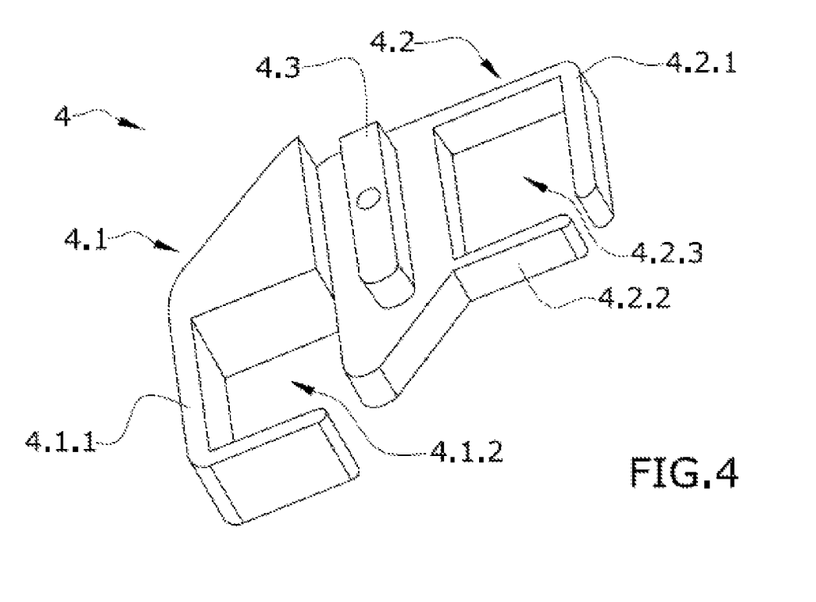
FIG. 4 shows a perspective view of the housing element according to an embodiment of the present invention.
Figure 5A:
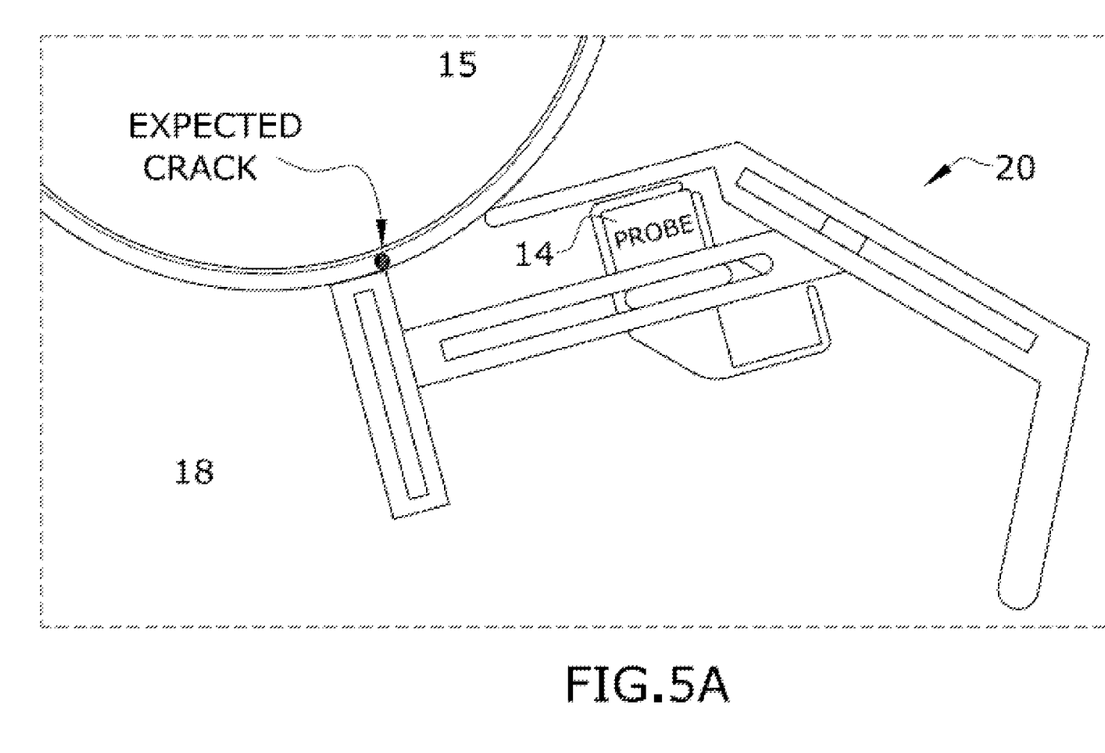
FIGS. 5A and 5B show another embodiment of the inspection device according to the present invention.
Figure 5B:
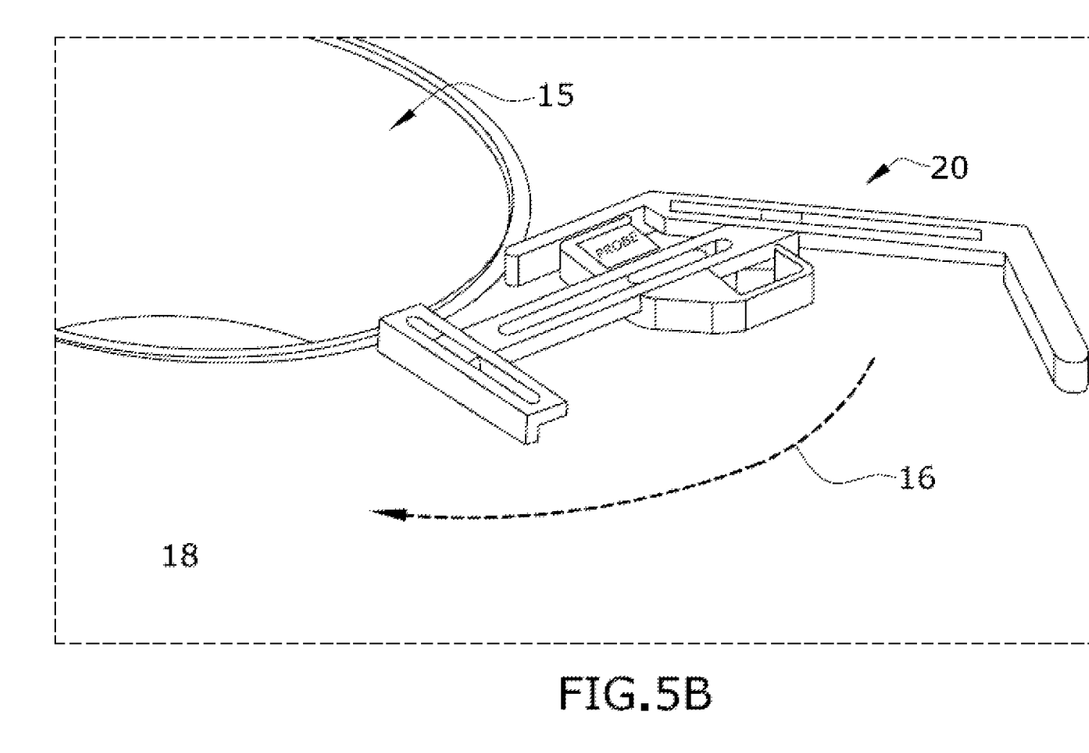

The housing element (4) is an interchangeable element that comprises a first housing part (4.1) and a second housing part (4.2), and is configured to house a probe (as it can be seen in FIGS. 4 and 5A-5B). The possibility to interchange the housing element (4) allows using different type and sizes of probes.

Additionally, as it can be seen in FIG. 4, the first housing part (4.1) comprises a U-shaped housing arm (4.1.1) extending from the first housing part (4.1). The U-shaped housing arm (4.1.1) defines a non-closed area (4.1.2).

In turn, the second housing part (4.2) comprises an L-shaped housing arm (4.2.1) and a housing arm (4.2.2), both extending from the second housing part (4.2). The L-shaped housing arm (4.2.1) and the housing arm (4.2.2) define a non-closed area (4.2.3).

Advantageously, the non-closed areas (4.1.2, 4.2.3) provide some flexibility and facilitate the positioning of the probe (14) in the housing element (4).

FIG. 1 shows one embodiment of the inspection tool (10) wherein the first lateral part (1.1) and the central part (1.2) forms an angle (A), and wherein the second lateral part (1.3) and the central part (1.2) forms an angle (B). In a particular embodiment the angle (A) is comprised between 100° and 115°, and the angle (B) is comprised between 125° and 145°. In a more particular embodiment, the angle (A) is 108°, and the angle (B) is 135° (as it can be seen in FIG. 1).

Figure 3:
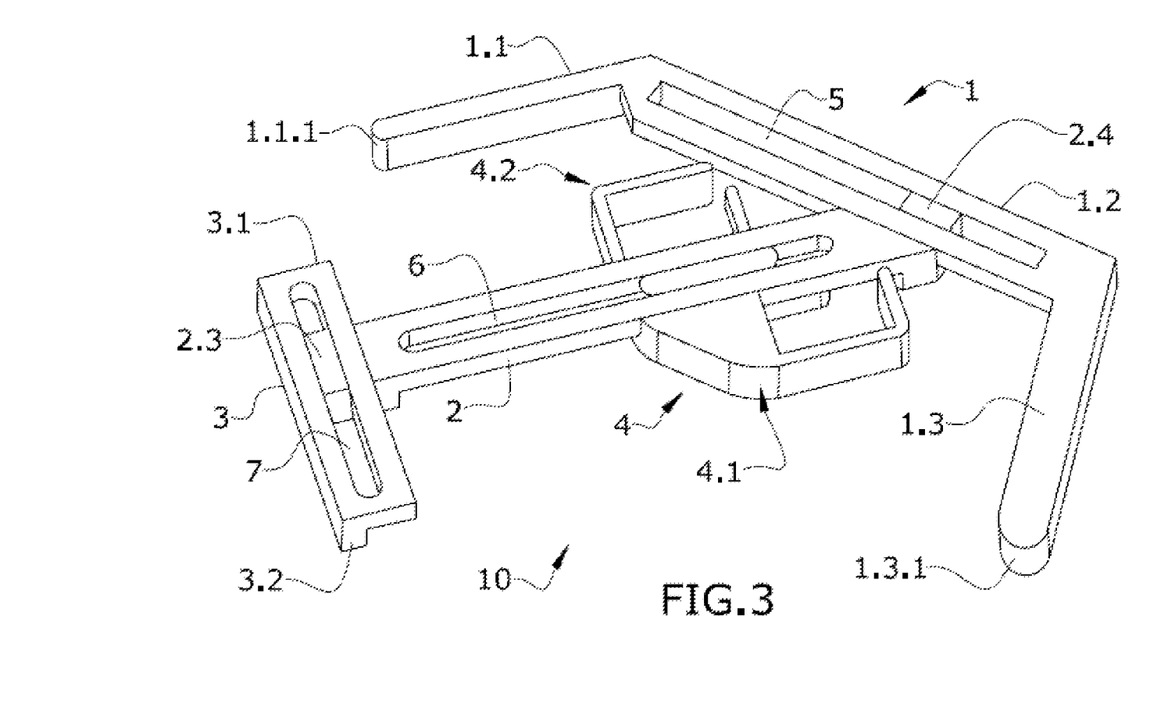
FIG. 3 shows another perspective view of the inspection tool according to the present invention without the fixing elements of each guiding projection.

FIG. 3 shows one embodiment of the inspection tool (10) wherein the second arm (2) comprises guiding projections (2.3, 2.4); and wherein the housing element (4) comprises a guiding projection (4.3). As it can be seen, the guiding projections (2.3, 2.4) are linked to the first arm (1) and third arm (3) through the guiding cavities (5, 7) of each first and third arms (1, 3) respectively. Additionally, the guiding projection (4.3) is linked to the second arm (2) through the guiding cavity (6) of the second arm (2). The guiding projections are configured to slide along the guiding cavities in order to allow the movement of each component (1, 2, 3, and 4) of the tool (10).

Thus, the first arm (1), third arm (3) and the housing element (4) may vary their position independently of each other in relation to the second arm (2).

Getting back to FIGS. 1 and 2, these figures show one embodiment of the inspection tool (10) wherein the guiding projections (2.3, 2.4, and 4.3) comprise, respectively, a fixing element (11, 12, and 13). These fixing elements (11, 12, 13) are configured to fix the guiding projections (2.3, 2.4 and 4.3) to the arms (1, 2, and 3).

FIG. 3 shows one embodiment of the inspection tool (10) without the fixing elements (11, 12, and 13) in order to observe details of each guiding projections (2.3, 2.4 and 4.3). These guiding projections (2.3, 2.4, and 4.3) are configured to slide along the guiding cavities (7, 5, and 6) respectively.

Additionally, as it can be seen in FIG. 1, the first arm (1) may vary its position in relation to the second arm (2) with a constant angle (C) formed between the central part (1.2) of the first arm (1) and the second arm (2). Also, the third arm (3) may vary its position in relation to the second arm (2) with a constant angle (D) formed between said second and third arm (2, 3).

In a particular embodiment the angle (C) is comprised between 100° and 115°. In a more particular embodiment, the angle (C) is 108°.

In an embodiment the angle (D) has a value of 90°. Advantageously, this angle (D) ensures the tangency between the inspection tool (10) and the lug's hole (15). Furthermore, said angle (D) ensures that the beam of the probe is perpendicular to the crack.

FIGS. 5A and 5B and 6A and 6B show one embodiment of an inspection device (20) for inspection of a metallic lug (18) that comprises an inspection tool (10) and a probe (14) wherein the inspection tool (10) is configured to be used depending on the diameter of the leg's hole to be inspected. The first arm (1) of the tool (10) comprises a first lateral part end (1.1.1) and a second lateral part end (1.3.1) which are configured to be in contact with the edge of the hole (15) of the metallic lug (18). Additionally, the third arm (3) of the tool (10) comprises a first and a second end (3.1, 3.2) which are configured to be in contact with the edge of the hole (15) of the metallic lug (18).

FIGS. 5A and 5B show an embodiment of the inspection device (20), wherein the tool (10) is located on the surface of the metallic lug (18), and wherein the first lateral part end (1.1.1) and the first end (3.1) are in contact with the edge of the hole (15). Also, the probe (14) is located in the second housing part (4.2) of the housing element (4).

Furthermore, FIGS. 5A and 5B show an example wherein the diameter of the lug's hole (15) is comprised between 15 and 100 mm. For this particular example, when the diameter of the hole (15) is comprised between 15 and 100 mm, the inspection device (20) is configured to work in the way that the first lateral part end (1.1.1) and the first end (3.1) are in contact with the edge of the hole (15). Thus, in this example, in order to detect cracks around the metallic lug, the inspection device (20) must be moved in a first direction (clockwise direction) (16) as it can be seen in FIG. 5B.

Figure 6A:
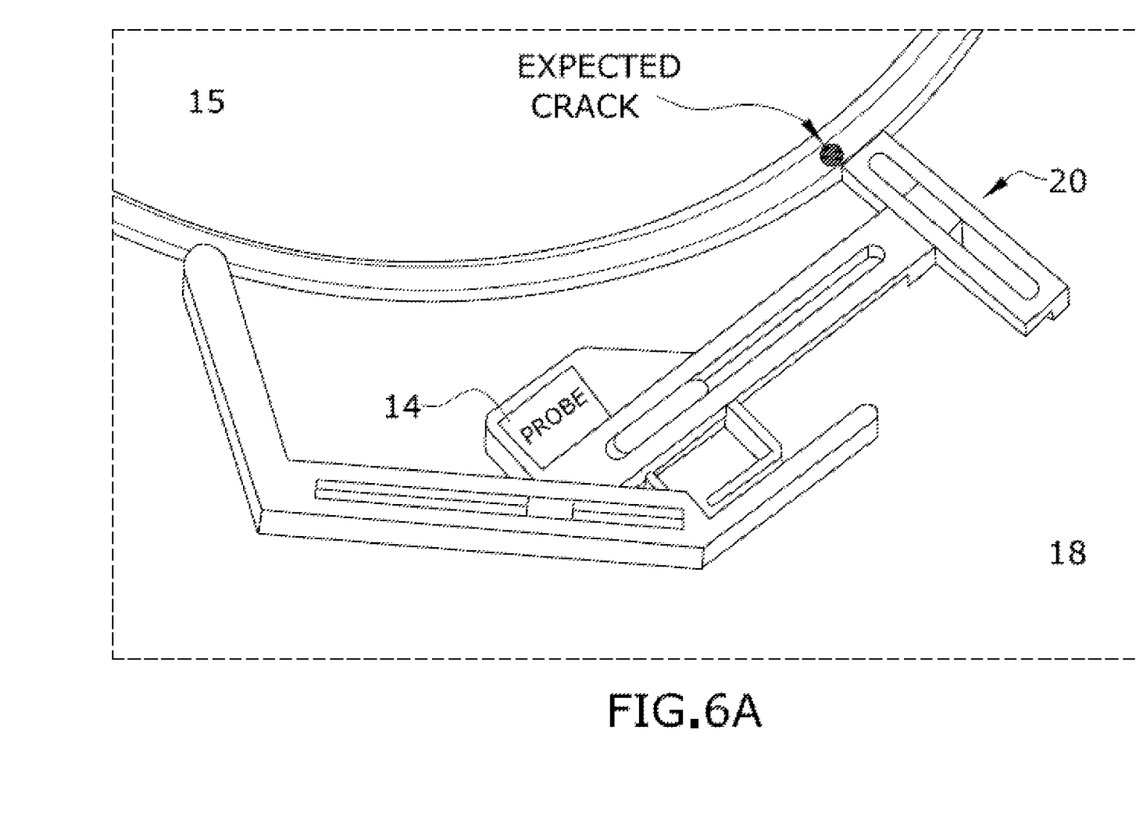
FIGS. 6A and 6B show another embodiment of the inspection device according to the present invention.
Figure 6B:
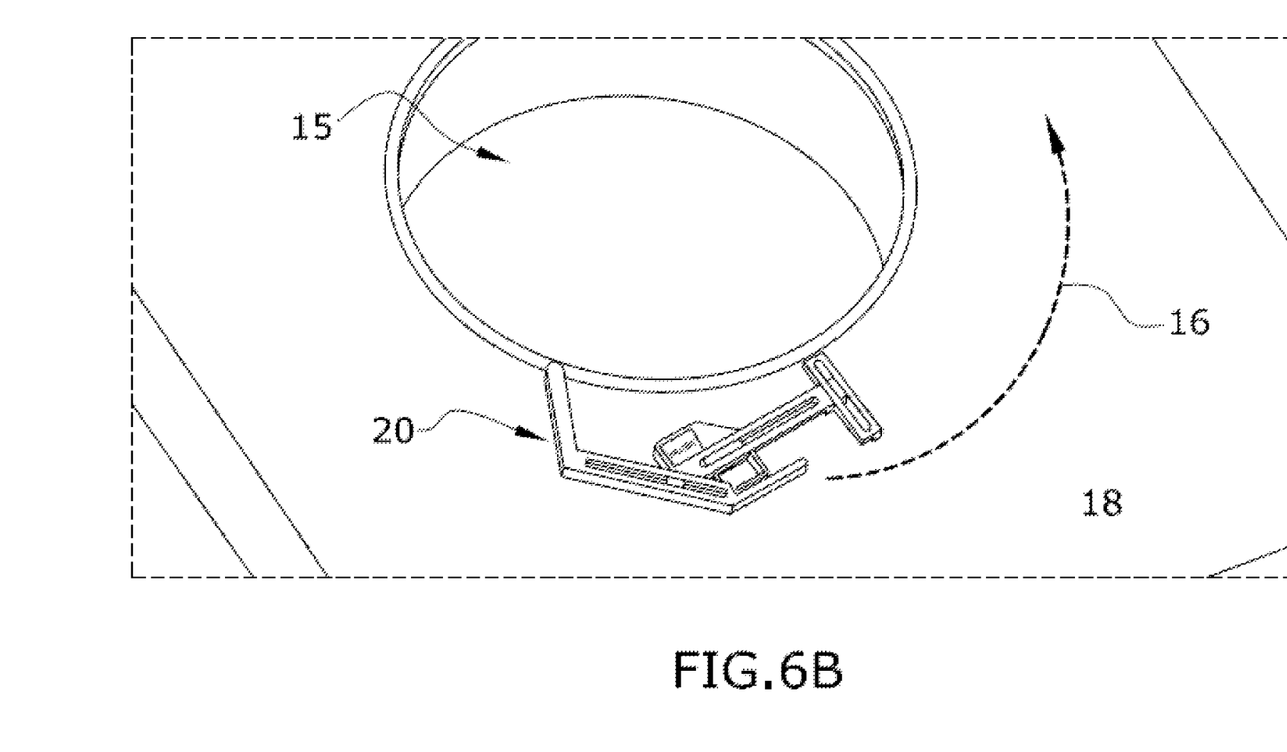

FIGS. 6A and 6B show one embodiment of the inspection device (20), wherein the tool (10) is located on the surface of the metallic lug (18), and wherein the second's lateral part end (1.3.1) and the second end (3.2) are in contact with the edge of the leg's hole (15). Also, the probe (14) is located in the first housing part (4.1) of the housing element (4).

Furthermore, FIGS. 6A and 6B shows an example wherein the diameter of the leg's hole (15) is comprised between 100 and 130 mm. For this particular example, when the diameter of the hole (15) is comprised between 100 and 130 mm, the inspection device (20) is configured to work in the way that second lateral part end (1.3.1) and the second end (3.2) are in contact with the edge of the hole (15). Thus, in this example, in order to detect cracks around the metallic lug, the inspection device (20) must be moved in a second direction (counter-clockwise direction) (17) as it can be seen in FIG. 6B.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. An inspection tool for inspection of a hole of a metallic lug, comprising,
   a first arm comprising:
      a first lateral part with a first lateral part end, the first lateral part end being configured to be in contact with the hole of the metallic lug,
      a central part, and
      a second lateral part with a second lateral part end, the second lateral part end being configured to be in contact with the hole of the metallic lug,
      the first lateral part and the central part forming a first angle,
      the second lateral part and the central part forming a second angle, and said central part comprising a first guiding cavity,
   a second arm comprising:
      a second guiding cavity, and
      two ends, wherein each of the two ends comprise respective first and second guiding projections,
   a third arm comprising:
      a third guiding cavity,
      a first end, and
      a second end,
      wherein the first end and the second end are configured to be in contact with the hole of the metallic lug, and
   a housing element comprising:
      a first housing part,
      a second housing part, and
      a third guiding projection,
   wherein the first arm, the third arm and the housing element vary their position independently of each other in relation to the second arm.

2. The inspection tool according to claim 1, wherein the first and second guiding projections of the second arm are linked to the first arm and third arm through the first and third guiding cavities of each of the first and third arms respectively, wherein the first and second guiding projections are configured to slide along respective ones of the first and third guiding cavities.

3. The inspection tool according to claim 1, wherein the third guiding projection of the housing element is linked to the second arm through the second guiding cavity of the second arm, wherein the second guiding projection is configured to slide along the third guiding cavity.

4. The inspection tool according to claim 1, wherein the housing element is an interchangeable element.

5. The inspection tool according to claim 1, wherein the first housing part and the second housing part of the housing element are configured to house a probe.

6. The inspection tool according to claim 1, wherein a position the first arm varies in relation to the second arm, wherein a third angle that is a constant angle is formed between a central part of the first arm and the second arm.

7. The inspection tool according to claim 1, wherein the third arm is configured to vary its position in relation to the seconds arm, wherein a fourth angle that is a constant angle is formed between the second and third arm.

8. The inspection tool according to claim 1, wherein the first angle is in a range of 100° to 115°.

9. The inspection tool according to claim 1, wherein each of the first, second and third guiding projections comprises a fixing element configured to fix the respective first, second and third guiding projections to the first, second and third arms respectively.

10. An inspection device for inspection of a metallic lug, comprising:
an inspection tool according to claim 1, and
a probe housed in any of the first and second housing parts of the housing element.

11. The inspection device according to claim 10 wherein the probe is an ultrasonic probe.

12. A method for detecting cracks at an edge of a hole in a metallic lug comprising:
measuring the diameter of the hole of the metallic lug,
providing an inspection device in a housing element of an inspection tool, wherein the inspection tool includes a first arm configured to contact the edge of the hole, a second arm slidably connected to the first arm and supporting the housing element, and a third arm slidably connected to the second arm and configured to contact the edge of the hole,
positioning the inspection device on surface of the metallic lug around the hole of the metallic lug,
sliding the inspection tool around the hole of the lug, and detecting cracks in the metallic lug at the edge of the hole.

13. The method for detecting cracks according to claims 12 further comprising applying a couplant on the surface of the metallic lug before the detection of the cracks.

14. An inspection tool and inspection device assembly configured for inspection of a hole of a metallic lug, the inspection tool and inspection device assembly comprising,
a first arm including a central part having a first guiding cavity, a first lateral part extending at a first angle that is an acute angle from a first end of the central part and a second lateral part extending from and at a second angle that is an acute angle from a second end of the central part, opposite to the first end, wherein the first and second lateral parts are configured to abut the hole;
a second arm having a first end slidably engaging the first guiding cavity of the first arm and a second end;
a housing element slidably engaged in a second guiding cavity in the second arm, wherein the housing element includes arms each configured to grasp the inspection device; and
a third arm having a third cavity configured to slidably engage the housing element, wherein the third arm has an end configured to abut the hole,
wherein a distance between the hole and the inspection device is adjustably set based on the slidable engagement between the second arm and each of the first arm and the third arm.

15. The inspection tool and inspection device assembly of claim 14 wherein the inspection device is an ultrasonic probe.

16. The inspection tool and inspection device assembly of claim 14 wherein the first arm, second arm and third arm are parallel to a plane and the inspection device projects a beam generally perpendicular to the plane.

* * * * *